US007959947B2

(12) United States Patent
Hölzer et al.

(10) Patent No.: US 7,959,947 B2
(45) Date of Patent: Jun. 14, 2011

(54) FILM COATING

(75) Inventors: Arne Hölzer, Mölndal (SE); Jan-Erik Löfroth, Mölndal (SE); Staffan Schantz, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 286 days.

(21) Appl. No.: 10/466,099

(22) PCT Filed: Jan. 22, 2002

(86) PCT No.: PCT/SE02/00103
§ 371 (c)(1),
(2), (4) Date: Jul. 11, 2003

(87) PCT Pub. No.: WO02/058677
PCT Pub. Date: Aug. 1, 2002

(65) Prior Publication Data
US 2004/0058001 A1    Mar. 25, 2004

(30) Foreign Application Priority Data

Jan. 24, 2001   (SE) .................................. 0100200

(51) Int. Cl.
*A61K 9/32* (2006.01)
*A61K 9/50* (2006.01)
*A61K 9/16* (2006.01)
*A61K 9/24* (2006.01)

(52) U.S. Cl. .......................... 424/482; 424/490; 424/473

(58) Field of Classification Search .................. 424/490, 424/473, 489, 482; 514/327
See application file for complete search history.

(56) References Cited

U.S. PATENT DOCUMENTS

| 3,341,338 | A | | 9/1967 | Pater |
| 3,371,015 | A | | 2/1968 | Sjogren et al. |
| 3,775,537 | A | | 11/1973 | Lehmann et al. |
| 4,330,338 | A | | 5/1982 | Banker |
| 4,353,887 | A | * | 10/1982 | Hess et al. ..................... 424/467 |
| 4,798,724 | A | | 1/1989 | Khanna |
| 4,800,087 | A | | 1/1989 | Mehta |
| 4,871,546 | A | | 10/1989 | Feltz et al. |
| 4,916,171 | A | | 4/1990 | Brown et al. |
| 4,927,640 | A | | 5/1990 | Dahlinder et al. |
| 4,957,745 | A | | 9/1990 | Jonsson et al. |
| 4,975,283 | A | | 12/1990 | Patell |
| 5,246,714 | A | | 9/1993 | Dahlinder et al. |
| 5,478,573 | A | * | 12/1995 | Eichel et al. ................. 424/480 |
| 5,484,597 | A | * | 1/1996 | Slavtcheff et al. ............ 424/401 |
| 5,594,013 | A | | 1/1997 | Trigger |
| 5,656,296 | A | * | 8/1997 | Khan et al. ..................... 424/473 |
| 5,681,584 | A | * | 10/1997 | Savastano et al. ............. 424/473 |
| 5,871,776 | A | | 2/1999 | Mehta ............................ 424/462 |
| 5,948,438 | A | * | 9/1999 | Staniforth et al. ............ 424/464 |
| 6,008,249 | A | | 12/1999 | Gajdos et al. |
| 6,030,988 | A | * | 2/2000 | Gilis et al. ..................... 514/327 |
| 6,046,177 | A | * | 4/2000 | Stella et al. ..................... 514/58 |
| 6,627,223 | B2 | | 9/2003 | Percel et al. |
| 6,827,947 | B2 | * | 12/2004 | Lofroth et al. ................ 424/497 |
| 2004/0030033 | A1 | | 2/2004 | Löfroth et al. |
| 2005/0089574 | A1 | * | 4/2005 | Lofroth et al. ................ 424/471 |
| 2005/0238719 | A1 | * | 10/2005 | Buzsaky ....................... 424/472 |
| 2005/0256255 | A1 | | 11/2005 | Karlsson et al. |

FOREIGN PATENT DOCUMENTS

| EP | 0 173 928 | 3/1986 |
| EP | 0 313 845 | 5/1989 |
| EP | 0 431 877 | 6/1991 |
| EP | 0 463 877 B1 | 1/1994 |
| EP | 0621032 | 10/1994 |
| GB | 0 878 234 | 9/1961 |
| WO | WO 96/11675 | 4/1996 |
| WO | WO 02/058677 | 8/2002 |

OTHER PUBLICATIONS

Lin et al. ("study of Crystallization of Endogenous Surfactant in EUDRAGIT NE30D-Free films and its Influence on Drug-Release Properties of controlled-Release Diphenhydramine HCI pellets coated with EUDRAGIT NE30D," in AAPS Pharmsci 2001: 3(2) article 14, provided by applicant in form 1449).*

Handbook of pharmaceutical excipients, 4th eddition, 2003 provided by applicant.*

Sandberg, A. et al., "Design of a New Multiple-Unit Controlled-Release Formulation of Metoprolol—Metoprolol CR", European Journal of Clinical Pharmacology (1988)33 [Suppl] S3-S7.

Ragnarsson, G. et al., "Development of a New Controlled Release Metoprolol Product", Drug Development and Industrial Pharmacy, 13(9-11), 1495-1509 (1987).

Z.M. Mathir et al., "In vitro characterization a controlled-release chlorpheniramine maleate delivery system prepared by the air suspension technique", *J. Microencapsulation*, 1997, vol. 14, No. 6, 743-751.

H-U Petereit et al., "Formulation and process consideration affecting the stability of solid dosage forms formulated with methacrylate copolymers", *European Journal of Pharmaceutics and Biopharmaceutics.*, 47 (1999) 15-25.

M. Wessling et al., "Tackiness of acrylic and cellulosic polymer films used in the coating of solid dosage forms", *European Journal of Pharmaceutics and Biopharmaceutics.*, 47 (1999) 73-78. A.Y. Lin et al., "Study of crystallization of endogenous surfactant in Eudragit NE30D-free films and its influence on drug release properties of controlled-release diphenhydramine HCI pellets coated with Eudragit NE #)D", *AAPS Pharmsci 2001*; 3(2) article 14.

* cited by examiner

*Primary Examiner* — Blessing M Fubara
(74) *Attorney, Agent, or Firm* — White & Case LLP

(57) ABSTRACT

A film coating composition suitable for use in coating pharmaceutical formulations comprising a) an acrylic polymer dispersion, e.g. an ethylacrylate/methylmethacrylate copolymer such as Eudragit NE30D, b) a surfactant, c) sodium stearyl fumarate, and d) a water-containing liquid useful for the achievement of controlled release from pharmaceutical formulations such as tablets, pellets, etc.

29 Claims, No Drawings

FILM COATING

This application is a 371 of PCT/SE02/000103, filed Jan. 22, 2002.

FIELD OF THE INVENTION

The present invention relates to a new film coating. More specifically the present invention relates to a new film coating for the achievement of controlled release from pharmaceutical formulations such as tablets, pellets, etc. wherein the film coating may be applied in a substantially aqueous environment. Furthermore, the invention provides a process for the preparation of such a film coating.

BACKGROUND OF THE INVENTION

Oral administration of a drug is the most convenient for the patient. Proper formulations must also meet the requirements of safety and simplicity. Depending on the properties of a drug and the therapeutic requirements different approaches must be taken during the formulation work to obtain the required delivery profile of the drug. Thus, sparingly soluble drugs to be given once a day require other types of formulations than easily soluble drugs to be taken several times a day. The matter has been discussed extensively in the literature and comprehensive reviews can be found, e g Langer and Wise (Eds) "Medical applications of controlled release", vols I and II, CRC Press Inc, Boca Raton, 1984; Robinson and Lee (Eds) "Controlled drug delivery—fundamentals and applications", Marcel Dekker, NY 1987; Bogeritoft and Sjögren, in "Towards better safety of drugs and pharmaceutical products" (Ed: Braimer), Elsevier, 1980; Sandberg "Extended-release metoprolol", Thesis, Uppsala University, 1994.

Different formulations have different mechanisms controlling the release of the active substance. In the thesis by Sandberg 1994, extended-release (ER) formulations of different types of drugs are reviewed. It is concluded that in principle two types of ER dosage forms exist; the matrix system where the drug is mixed with the matrix material (often a polymer or a wax); and the drug reservoir system where the drug is formulated into a core (tablet or pellets) surrounded by a polymeric film. The film is then a release rate-controlling barrier determined by, e g its dissolution rate, its permeability, the solubility of the substance, etc.

From a flexibility point of view the formulation of a drug into small discrete units coated with a film has gained much attention. Such formulations show several interesting features, e g flexibility in dosage and modification of release properties, different dosage forms can be developed, dose size is adaptable to suit fixed combinations, tablets can be made divisible etc. In a number of studies it was shown that safe, simple, and convenient therapy could be achieved utilising this principle for the drug metoprolol and its salts (Ragnarsson et al, *Drug Develop Ind Pharmacy* 13, 1495 (1987); Sandberg et al, *Eur J Clin Pharmacol* 33, S3 (1988) and S9 (1988); Ragnarsson et al, *Int J Pharmaceutics* 79, 223 (1992); Sandberg et al, *Ibid* 68, 167 (1991); Sandberg et al, *Pharmaceutical Res* 10, 28 (1993); Sandberg et al, *Drug Invest* 6, 320 (1993); Sandberg, *Thesis* Uppsala University, 1994).

The formulation of metoprolol into pellets according to the above mentioned references utilised a film coating sprayed from a solution of ethyl cellulose and hydroxypropyl methyl cellulose in an organic solvent. However, for environmental reasons it will be necessary in the near future to utilise water based film forming systems for this and other drugs to be formulated as pellet systems. Also, tablet coatings in general utilising organic solvents must for the same reasons be exchanged with water based film forming materials. Thus, much effort has been directed to find suitable water based systems for film coatings in drug delivery systems.

Latex particles in water as the dispersion medium have been known for almost half a century. These particles are polymeric colloidal particles in the 10 to 1000 nm range and have been utilised as film formers, e g in paints, in floor coatings, printing inks, adhesives etc. If the particle polymer has a sufficiently low glass transition temperature (Tg) when the water is evaporated, the particles can coalesce to form a film.

Water based film-forming polymer latexes for the pharmaceutical industry have been known since the early eighties when commercial dispersions more frequently appeared on the market (e g Aquacoat, FMC Corp.; Eudragit E-30D, Röhm Pharma). Further development has given several other products that have been tested and reported in a number of publications (Petereit and Weisbrod, *Eur J Pharmaceutics and Biopharm* 47, 15 (1999); Petereit et al, *Ibid*, 41, 219 (1995); Amighi and Moës, *STP Pharma Sci* 7, 141 (1997); Bodmeier and Paeratukul, *Pharm Res* 11, 882 (1994); Ozturk et al, *J Controlled Release* 14, 203 (1990). Goodhart et al, *Pharmaceutical Tech* April, 64 (1984); Bodmeier and Paeratakul *Int J Pharmceutics* 152, 17 (1997); Bodmeier and Paeratakul *Drug Develop Ind Pharmacy* 20, 1517 (1994)).

From these and other studies it can be concluded that one of the more interesting dispersions, due to the low Tg of the latex polymer, is Eudragit® NE30D, which contains approximately 28.5% w/w particles of the copolymer poly(ethylacrylate—co-methylmethacrylate), and 1.5% w/w of the non-ionic tenside Nonoxynol 100 (a polyoxyethylated nonylphenol) as the stabiliser. However, to obtain best spraying conditions and technical appearance of the film-coated pellets, an anti-sticking agent has to be added to the dispersion as reported by Petereit and Weisbrod 1995. One such agent is a glyceryl monostearate (GMS). It was also reported, however, that best performance of the dispersion during spraying and of the dried film was obtained when the GMS was dispersed with an extra surface active agent, e g polysorbate 80 (PS80). On the other hand, we have found that it has been difficult to obtain results with acceptable reproducibility with respect to, e g permeability and release rates from formulations manufactured according to these suggested procedures. One tentative explanation for this might be that the properties of the GMS/PS80 dispersion, e g size of dispersed particles, highly depend on process parameters like temperature, type of mixing etc, which also can be concluded from the results in the paper by Petereit and Weisbrod 1995.

Anti-sticking agents, also named detackifiers, glidants, and lubricants, are well-known agents used during pharmaceutical work. Similar substances have been used as anti-caking agents in food industry. The most commonly used substances for these purposes are, e g stearates, talc, polyethylene glycols, paraffines, lauryl sulphates, silica, and starches (M E Aulton (Ed) *Pharmaceutics—the science of dosage form design* Churchill Livingstone 1988; Susan Brewer *Food Additives*, document EHE-677 Illinois Co-operative Extension Service, 1994; M Ash and I Ash (Eds) *Handbook of Pharmaceutical Additives*, Gower Publishing Ltd, 1995). In connection with film-forming dispersions the most popular anti-sticking agents seem to be GMS, talc, and silica. However, in most of these latter applications reported these substances must first be dispersed with other added material, preferably surfactants or amphiphilic polymers to obtain more homogeneous systems.

Several patents or patent applications utilising these principles exist. Thus, Wolff et al, WO 00/13687; Wolff et al, WO 00/13686; Nagy et al, WO 99/42087; Lee et al, WO 99/30685; Eichel et al, U.S. Pat. No. 5,529,790; Eichel U.S. Pat. No. 5,478,573; Chen, U.S. Pat. No. 5,260,068; Petereit et al, EP 403,959; disclose the use of Eudragits for the (controlled) release of different types of drugs. In those applications when anti-sticking agents have to be used, combinations of surface active molecules and talc or stearates are most common. However, for our purposes these approaches are not attractive since several problems may arise due to, e g the combination of non-compatible materials, large amounts of extra dispersion additives, non-reproducibility during manufacturing, etc.

Sodium stearyl fumarate (sodium salt of 2-butenedioic monooctadecyl ester; Pruv™) is a pharmaceutical additive normally used as a lubricant for tabletting, where it in many cases can substitute and is superior to, e g magnesium stearate (*Handbook of Pharmaceutical Excipients* (Eds: A Wade and P J Weller) 2nd edition, Pharmaceutical Press, London 1994; A W Hözer and J Sjögren *Int J Pharmaceutics* 2, 145 (1979); G K Bolhuis and A W Hölzer in *Pharmaceutical powder compaction technology* (Eds G Aldeborn and C Nyström), Marcel Dekker Inc, NY 1995, chapter 16). Also, Pruv is approved for several food applications (*Code of Federal Regulations*, title 21, volume 3, part 172). Its solubility in water can be described by 1 g (solubility (gram Pruv/gram water))=0.057*T/(° C.)−5.7 according to the data given in the *Handbook*. Thus, at e g 60° C. the solubility is 0.005 gram per gram water. Further, its HLB value calculated according to the method by Davies (B Jönsson, B Lindman, K Holmberg, and B Kronberg *Surfactants and polymers in aqueous solutions* John Wiley & Sons, Chichester, 1998 p 353) amounts to about HLB=19.

PURPOSE OF THE INVENTION

The purpose of the present invention is to provide a new film coating system that does not have the above mentioned problems. Improved properties of the new film coating system are, for example, non-stickiness, reproducibility during processing and a minimal addition of extra additives to the dispersion before the film forming process. Another aspect of the invention is to provide a method of manufacturing coated formulations, for example pellets or tablets, utilising this new film forming system.

SUMMARY OF THE INVENTION

We have now surprisingly found a novel film coating composition which provides a latex dispersion suitable for coating pharmaceutical formulations wherein the film produced serves as a barrier giving close to constant release (zero-order) from the formulation. In addition the physical properties of the film produced were such that no processing problems, for example adhesion, were experienced.

The present invention provides a film coating composition suitable for use in coating pharmaceutical formulations comprising
a) an acrylic polymer dispersion
b) a surfactant
c) sodium stearyl fumarate and
d) a water-containing liquid.

DETAILED DESCRIPTION OF THE INVENTION

In another aspect the invention provides a film coat covering a pharmaceutical core wherein the core comprises a pharmacologically active ingredient and optionally one or more pharmaceutically acceptable excipients wherein the film coat comprises
a) an acrylic polymer
b) a surfactant and
c) sodium stearyl fumarate,
wherein the film coat has been deposited from a water-containing liquid.

Suitably the film coat has a thickness in the range of 1 to 100 micrometers, preferably in the range of 5 to 50 micrometers and more preferably in the range of 10 to 30 micrometers.

In another aspect the invention provides a pharmaceutical formulation comprising
a) a pharmaceutical core comprising a pharmacologically active ingredient and optionally one or more pharmaceutically acceptable excipients and
b) a film coat comprising
i) an acrylic polymer
ii) a surfactant and
iii) sodium stearyl fumarate,
wherein the film coat has been deposited from a water containing liquid.

In a preferred aspect of the invention the pharmacologically active ingredient is provided in a plurality of beads optionally containing one or more pharmaceutically acceptable excipients wherein each of the beads is coated with a film coat as defined above. Such film coated beads may be provided in sachets or formulated as a capsule, for example a hard gelatin capsule, or compressed to form tablets using known methods with the optional addition of other pharmaceutically acceptable additives. Coated beads to be compressed into a tablet are obtained by conventional techniques known to those skilled in the art.

Also, during this process suitable other agents can be added. For example, during the tabletting step suitable fillers, eg microcrystalline cellulose, talc. sodium stearyl fumarate etc can be utilised to give acceptable compression characteristics of the formulation, e g hardness of the tablet.

Suitably the beads have a diameter in the range of 0.01-2 mm. preferably in the range of 0.05-1.0 mm and more preferably in the range of 0.1-0.7 mm.

Optionally the beads may contain an insoluble core onto which the active ingredient has been deposited for example by spraying. Suitable materials for the inert core are silicon dioxide, glass or plastic resin particles. Suitable types of plastic material are pharmaceutically acceptable plastics such as polypropylene or polyethylene preferably polypropylene. Such insoluble cores have a size diameter in the range of 0.01-2 mm, preferably in the range of 0.05-0.5 mm and more preferably in the range of 0.01-0.3 mm.

In a more preferred aspect the present invention provides a controlled release formulation wherein the pharmacologically active ingredient is controlled over a long period of time, for example 8 to 24 hours preferably 20 to 24 hours, in comparison to an immediate release tablet.

Preferably the pharmacologically active ingredient has activity in the treatment of cardiovascular and gastrointestinal diseases. In particular the pharmacologically active ingredient is a beta-blocking adrenergic agent. The beta-blocking adrenergic agents referred to in this application include but are not limited to the compounds selected from the group consisting of acebutolol, alprenolol, amosulalol, arotinolol, atenolol, befunolol, betaxolol, bevantolol, bisoprolol, bopindolol, bucumolol, bufetolol, bufuralol, bunitrolol, bupranolol, butofilolol, carazolol, carteolol, carvedilol, celiprolol, cetamolol, cloranolol, dilevalol, epanolol, indenolol, labetalol, levobunolol, mepindolol, metipranolol, metoprolol, moprolol, nadolol, nadoxolol, nebivalol, nipradilol, oxprenolol, perbutolol, pindolol, practolol, pronethalol, propranolol, sotalol, sufinalol, talindol, tertatolol, tilisolol, timolol, toliprolol, and xibenolol, and stereoisomers thereof and pharmaceutically acceptable salts or solvates thereof, or solvates of such salts. A preferred beta-blocking adrenergic agent is metoprolol or a pharmaceutically acceptable salt thereof.

Alternatively the pharmacologically active ingredient is a cholesterol-lowering agent including but not limited to an HMG-CoA (3-hydroxy-3-methylglutaryl coenzyme A) reductase inhibitor. The HMG-CoA reductase inhibitor may be a statin selected from atorvastatin, bervastatin, cerivastatin, dalvastatin, fluvastatin, itavastatin, ivastatin, lovastatin, mevastatin, nicostatin, pravastatin, rivastatin, rosuvastatin and simvastatin. Particularly preferred statins are, however, those disclosed in European Patent Application No. EP-A-0114027, or a pharmaceutically acceptable salt, especially sodium, or solvate thereof, or a solvate of such a salt, and a compound with the chemical name (E)-7[4-(4-fluorophenyl)-6-isopropyl-2-[methyl(methylsulfonyl)-amino]-pyrimidin-5-yl](3R,5S)-3,5-dihydroxyhept-6-enoic acid, and salts thereof such as its calcium and sodium salts are disclosed in European Patent Application, Publication No. EP-A-0521471, and in Bioorganic and Medicinal Chemistry, (1997), 5(2), 437-444.

In the present patent application, the term "cholesterol-lowering agent" includes chemical modifications, such as esters, stereoisomers, prodrugs and metabolites, whether active or inactive, and pharmaceutically acceptable salts or solvates of any of these, or solvates of such salts.

The pharmaceutical formulations of the present invention may be used to treat cardiovascular and gastrointestinal diseases.

In yet another aspect the invention provides a controlled release metoprolol formulation comprising
a) a metoprolol core comprising metoprolol or a pharmaceutically acceptable salt thereof and optionally one or more pharmaceutically acceptable excipients and
b) a film coat as defined above.

In a preferred aspect the core comprising metoprolol or a pharmaceutically acceptable salt thereof comprises a plurality of beads which comprise metoprolol or a pharmaceutically acceptable salt thereof and optionally one or more pharmaceutically acceptable excipients wherein each of the beads is coated with a film-coat as defined above. Preferably the beads have an inert core as described previously.

Suitable pharmaceutically acceptable salts of metoprolol include the tartrate, succinate, fumarate or benzoate salts and especially the succinate salt. The S-enantiomer of metoprolol or a salt thereof, particularly the benzoate salt or the sorbate salt, may also be used.

The term acrylic polymer dispersion as used herein means a polymer, or copolymer comprising two or more, of the following monomers: acrylic acid and esters thereof particularly the methyl, ethyl, propyl and butyl esters; and methacrylic acid and esters thereof particularly the methyl, ethyl, propyl and butyl esters, which is dispersed in a substantially aqueous liquid preferably water. Also hydroxylated acrylic and methacrylic esters are included.

In one aspect the present invention provides film coatings which are suitable for giving extended release. Suitably the acrylic polymer dispersion used in this case comprises homogeneous particles wherein the polymer or copolymer has a $T_g$<room temperature for example acrylate and/or methacrylates such as a methyl acrylate/methyl methacrylate copolymer or a butyl acrylate/methyl methacrylate copolymer. One group of preferred acrylic polymers for this use comprises an ethyl acrylate/methyl methacrylate copolymer for example Eudragit® NE30D in which the ethyl acrylate concentration is about 67 mol % or an ethyl acrylate/methyl methacrylate copolymer described in the Journal of Applied Polymer Science 1970, 14, 73-78 in which the ethyl acrylate concentration is greater than 50 wt %.

Alternatively the acrylic polymer dispersion used to obtain extended release suitably comprises heterogeneous particles comprising a core polymer or copolymer and a shell polymer or copolymer wherein the shell polymer or copolymer has a $T_g$<room temperature, for example a butyl acrylate polymer, and the core polymer or copolymer has a Tg>room temperature. Preferably the shell polymer comprises acrylate and/or methacrylate polymers or copolymers wherein the Tg is less than room temperature. More preferably the shell polymer is an ethyl acrylate polymer.

In another aspect the present invention provides film coatings which are suitable for providing an enteric coating. Suitably the acrylic polymer used in this case comprises homogeneous particles wherein the polymer or copolymer has $T_g$<room temperature in aqueous dispersion but has $T_g$>room temperature in the dry state. Suitable polymers comprise acrylic acid and esters thereof particularly the methyl, ethyl, propyl and butyl esters; and methacrylic acid and esters thereof particularly the methyl, ethyl, propyl and butyl esters. Particularly preferred polymers are those provided under the tradenames Eudragit L30D® (Röhm Pharma) or Eudragit FS30D® (Röhm Pharma). Optionally further anti-tacking agents may be required.

Suitably the amount of the acrylic polymer in the film coating composition is in the range of 15 to 50% by weight. Preferably the amount of the acrylic polymer in the film coating composition is in the range of 20 to 40% by weight. More preferably the amount of the acrylic polymer in the film coating composition is in the range of 25 to 35% by weight.

Suitably the amount of the acrylic polymer in the film coat is in the range of 80 to 99.5% by weight. Preferably the amount of the acrylic polymer in the film coat is in the range of 85 to 99% by weight. More preferably the amount of the acrylic polymer in the film coat is in the range of 85 to 95% by weight.

Suitably the surfactant is one of the following:
a nonionic surfactant, like sorbitan esters (Span series); polysorbates (Tween series); polyoxyethylated glycol monoethers (like the Brij series); polyoxyethylated alkyl phenols (like the Triton series or the Igepal series); alkyl glucosides (e g dodecylmaltoside); sugar fatty acid esters (e g sucrose laurate); saponins; etc: or mixtures thereof;
ampholytic surfactants, like betaines;
anionic surfactants, like sulphated fatty alcohols eg sodium dodecylsulphate SDS; sulphated polyoxyethylated alcohols; others like dioctyl sulphosuccinate; bile salts (e g dihydroxy bile salts like sodium deoxycholate, trihydroxy bile salts like sodium glycocholate, etc); fusidates (e g sodium dihydrofusidate); etc
cationic surfactants, like ammonium compounds;
soaps, fatty acids, and lipids and their salts, like alkanoic acids; (e g octanoic acid, oleic acid); monoglycerides (eg monolein), phospholipids which are neutral or positively or negatively charged (eg dialkyl phosphatidylcholine, dialkyl phosphatidylserine, etc); etc;
More preferably the surfactant is a nonionic surfactant. Most preferably the surfactant is nonoxynol 100.

Suitably the amount of the surfactant in the film coating composition is in the range of 0.05 to 8% by weight. Preferably the amount of the surfactant in the film coating composition is in the range of 0.1 to 6% by weight. More preferably the amount of the surfactant in the film coating composition is in the range of 0.5 to 4% by weight.

Suitably the amount of the surfactant in the film coat is in the range of 0.05 to 12% by weight. Preferably the amount of the surfactant in the film coat is in the range of 2 to 10% by weight. More preferably the amount of the surfactant in the film coat is in the range of 4 to 8% by weight.

In a most preferred embodiment of the present invention the acrylic polymer and the surfactant are provided by Eudragit® NE30D in compositions, a film coats or formulations defined previously.

Sodium stearyl fumarate (alternatively known as the sodium salt of 2-butenedioic monooctadecyl ester) is available from Penn-West Pharmaceuticals under the tradename PRUV®.

Suitably the amount of the sodium stearyl fumarate in the film coating composition is in the range of 0.05 to 8% by weight. Preferably the amount of sodium stearyl fumarate in the film coating composition is in the range of 0.1 to 6% by weight. More preferably the amount of sodium stearyl fumarate in the film coating composition is in the range of 0.5 to 4% by weight.

Suitably the amount of sodium stearyl fumarate in the film coat is in the range of 0.05 to 12% by weight. Preferably the amount of sodium stearyl fumarate in the film coat is in the range of 2 to 10% by weight. More preferably the amount of sodium stearyl fumarate in the film coat is in the range of 4 to 8% by weight.

Suitably the water-containing liquid comprises water and a water miscible organic liquid for example lower alkanols e.g. ethanol, propanol or isopropanol. From a safety point of view is preferred that the proportion of the organic is kept to a minimum but small amounts are tolerable for example in the range of 0 to 20% by volume. Preferably the liquid is water.

The film-coating composition is particularly suitable for use as an aqueous film-coating composition wherein the film-coat is applied using water as the liquid. When the liquid is water the latex is preferably a poly(ethylacrylate-co-methylmethacrylate) copolymer, for example Eudragit NE30D® (Röhm Pharma). This process is particularly advantageous as it negates the need to use environmentally unacceptable organic solvents, some of which also present processing problems due to their inflammablility, while also eliminating many of the problems experienced with aqueous coatings described above.

In another aspect the present invention provides processes for the preparation of the film-coating composition. Therefore there is provided a process for the preparation of a film-coating composition comprising mixing together the acrylic polymer dispersion, the surfactant, sodium stearyl fumarate and the liquid at a temperature in the range of 10 to 100° C.

In one embodiment of the process the acrylic polymer dispersion, the surfactant, sodium stearyl fumarate and the liquid are mixed at room temperature and then slowly heated, while stirring carefully, to the desired temperature, preferably about 60° C. After a couple of minutes the mixture is then slowly cooled, while stirring carefully, to room temperature before film preparation by, for example, spraying.

In another embodiment, sodium stearyl fumarate is first mixed with the liquid and slowly heated to the desired temperature, preferably about 60° C., while carefully stirring the mixture. After a couple of minutes, the acrylic polymer dispersion and the surfactant are then added, the stirring continued for a couple of minutes, and the mixture cooled as above.

In yet another embodiment, sodium stearyl fumarate, the acrylic polymer dispersion and the surfactant are first mixed and heated to the desired temperature, preferably about 60° C., while stirring carefully. The liquid, which can be preheated or not, is then added and the mixture then handled as above.

Other protocols than these typical general approaches are possible. Thus, for example the temperature during the mixing of the components is preferably about 60° C. However, other temperatures, higher or lower can be chosen to meet special requirements in different applications. Lower temperatures will give larger particles of sodium stearyl fumarate in the mixtures when cooled to room temperature. Higher temperatures can be chosen and are recommended when high contents of sodium stearyl fumarate are required. Also, other additives, e g extra surfactant, colours etc can be added at any time during the process.

Suitably mixing is achieved by methods such as stirring or shaking but other methods of homogenization known to those skilled in the art may be used.

In another aspect the present invention provides a process for film coating a pharmaceutical core wherein a film coating composition as defined above is applied to a core. Preferably the film coating composition is applied by spraying for example in a fluidised bed with top spray or bottom spray techniques. Other coating methods used are coating in standard coating pans with perforated pans, Accela-cota, immersion swords, Glatt, or immersion tubes as described in "Theory and Practice in Industrial Pharmacy" edited by Lachman, published by Lea and Feabiger 1986 $3^{rd}$ edition.

In another aspect the invention provides a process to prepare a film coat as defined above comprising removing the liquid from a film coating composition as defined above. Suitably the liquid is removed by evaporation for example by spray drying for example in a fluidised bed. When coating the tablets in a standard coating pan, hot air is used for drying.

In yet another aspect the invention provides a process to prepare a formulation as defined above comprising coating a pharmaceutical core as defined above with a film coating composition as defined above.

In a further aspect the invention provides a process to prepare a formulation in which the pharmacologically active ingredient is provided as a plurality of beads as defined above comprising coating the plurality of beads with a film-coating composition as defined above.

Typically a film coating composition comprises
a) 25 to 35% by weight of an acrylic polymer dispersion
b) 0.1 to 4% by weight of a surfactant
c) 0.1 to 4% sodium stearyl fumarate and
d) a water-containing liquid to 100%.

EXAMPLES

The following examples are non-limiting and are given by way of illustration only. It will be appreciated by those skilled in the art that the examples are to be looked upon as guidelines, and the invention is not restricted to the exemplified compositions. A wide range of combinations is possible to give film coatings having the necessary properties required for each specific application.

Example 1

Preparation of Free Films from Sodium Stearyl Fumarate and NE30D®

Three mixtures of sodium stearyl fumarate and NE30D® were prepared at room temperature accordingly:

A: 10.323 g NE30D®+0.0149 g sodium stearyl fumarate+ 3.75 ml H$_2$O (giving 0.11% w/w sodium stearyl fumarate, with sodium stearyl fumarate/particle ratio approximately 0.5%);

B: 10.278 g NE30D®+0.0304 g sodium stearyl fumarate+ 3.75 ml H$_2$O (giving 0.22% w/w sodium stearyl fumarate, with sodium stearyl fumarate/particle ratio approximately 1%);

C: 10.407 g NE30D®+0.0508 g sodium stearyl fumarate+ 3.75, ml H$_2$O (giving 0.35% w/w sodium stearyl fumarate, with sodium stearyl fumarate/particle ratio approximately 1.6%);

The mixtures were heated slowly to 60° C. while gently stirring. After 2 minutes, the dispersion was cooled (no heating) to room temperature while gently stirring. Free films (10×10 cm$^2$) of the three dispersions were obtained by pouring approximately 10 ml of each dispersion in Teflon moulds, which were set aside at 25° C., 60% relative humidity for drying and film-formation during 18 hrs.

Results:

The stickiness of the films was tested by simple manual handling of the films. The best non-sticky film was judged to have been obtained from dispersion mixture C. Therefore, this film was tested in a permeability experiment, as described in Example 2.

Comparative Example 1

Preparation of Films from GMS/PS80/NE30D

Three mixtures of GMS, PS80 and NE30D® were prepared. Different mixing conditions of GMS and PS80 were used to examine the influence of the stirring rate. Thus, first GMS and PS80 were mixed according to either D, E, or F below. Then, appropriate amounts of this dispersion were added to NE30D® to give the intended compositions. The same amounts of GMS, PS80, and NE30D® were used, namely 0.225 g GMS, 0.090 g PS80, and 15.0 g NE30D which gave dispersions with 1.5% w/w GMS (GMS/particle ratio=5%). This composition was taken from the paper by Petereit and Weisbrod 1995.

D: 1 hour; homogenizer at 6000 rpm; 65° C.;
E: 20 min; homogenizer at 3000 rpm; 65° C.;
F: 4 hours; magnet stirring; 65° C.

Free films (10×10 cm$^2$) of the three dispersions were obtained by pouring approximately 10 ml of each dispersion in Teflon moulds, which were set aside at 25° C., 60% relative humidity for drying and film-formation during 18 hrs.

Example 2

Permeability of Free Films

Pieces of the films C, D, E, and F prepared according to Examples 1 (film C) and Comparative Example 1 (films D, E, F) were mounted in diffusion chambers consisting of two chambers separated by a free film (Hjärtstam, Thesis, Chalmers University of Technology, Göteborg 1998). The transport of labelled water was followed from the donor side to the receiver side over the membrane at 25° C. Appropriate volumes were taken from the receiver side at different times. The permeability of a film was calculated from the slope of the data of transported amount of labelled water vs time.

Results:

The results from the permeability experiments are shown in Table 1. It is seen that highly variable permeability was obtained with the three GMS/PS80/NE30D dispersions. However, the trend in the data suggested that a protocol which produced better dispersed GMS particles gave a lower permeability (D better than E better than F). Nevertheless, it was not possible to obtain the low permeability shown by Film C obtained from the sodium stearyl fumarate/NE30D dispersion according to this invention. Moreover, the permeability of Film C was comparable to what could be expected with a free film typical for the organic solvent based film (G) used for coating of the drug metoprolol (Lindstedt, Ragnarsson, and Hjärtstam, *Int J Pharmaceutics* 56, 261 (1989). Thus, superior quality of free film could be obtained with the present invention with only one additive and under very simple processing (gentle stirring during 2 minutes at 60° C.) before film-preparation.

TABLE 1

Permeability of free films

| | Film | | | | |
|---|---|---|---|---|---|
| | C | D | E | F | G |
| Permeability (m$^2$ s$^{-1}$ × 10$^{12}$) | 1.8 | 30.1 | 40.5 | 51.0 | >1.8 (1.8-10) |

Example 3

Preparation of Coated Metoprolol Succinate Pellets

Film coating on metoprolol succinate pellets (size fraction 0.40-0.63 mm, with inert silicon dioxide cores) was carried out on a laboratory-scale, fluid-bed Wurster apparatus. Two mixtures were prepared as coating solutions:

A: 0.916 g sodium stearyl fumarate was added to 67.59 g water. 186.62 g of NE30D was then added (giving 0.36% w/w sodium stearyl fumarate, with a sodium stearyl fumarate/particle ratio approximately 1.6% assuming that NE30D contains 30% particles). The mixture was heated slowly to between 57-60° C. while gently stirring. After 2 minutes, the mixture was allowed to cool (no heating) to room temperature while gently stirring.

B: 1.86 g sodium stearyl fumarate was added to 67.08 g water. 186.31 g of NE30D was then added (giving 0.73% w/w sodium stearyl fumarate, with a sodium stearyl fumarate/particle ratio approximately 3.3% assuming that NE30D contains 30% particles). The mixture was heated slowly to 61° C. while gently stirring. After 5 minutes, the mixture was allowed to cool (no heating) to room temperature while gently stirring.

The coating conditions were as follows:

| | |
|---|---|
| Bed weight | 200 g |
| Coating solution | ~170 g |
| Spraying rate | 5.3 g/min |
| Atomising air pressure | 2.5 bar |
| Fluidising air flow rate | 35 m$^3$/h |
| Inlet air temp. | 30° C. |
| Outlet air temp. | 20° C. |

The coating pellets were then dried in the fluid-bed, 40° C. (approx. 20 min.). During this step the fluidising air flow rate was kept at approximately 20 m$^3$/h.

Results: No problems, e g sticking of pellets, were met during the process.

Example 4

Release of Metoprolol from Coated Pellets

The release of metoprolol from about 100 mg pellets made according to Example 3 was studied at 37° C. using the USP dissolution apparatus II (rotating paddle) with stirring rate=100 rpm. The release medium was composed of phosphate buffer with the ionic strength=0.1 M and the pH=6.8. Samples were withdrawn for analysis (absorbance of metoprolol at 273 nm in a 1 cm cell). Amounts of released metoprolol were determined from measurements of the absorbance of a standard metoprolol solution based on the same medium as used in the release experiments.

Results: The amounts of released metoprolol vs time are given in Table 2 referring to the different coating solutions A and B made according to Example 4. It is seen that a close to constant release of metoprolol from the coated pellets was obtained during most of the time for both preparations after an initial lag time phase. Fastest release was observed from pellets coated with a coating solution containing more sodium stearyl fumarate (preparation B). The reason for the low standard deviation (SD) in the second experiment was attributed to the fact that the release studies in this case were carried out with an automatic instrument set-up.

TABLE 2

Release (%) of metoprolol from coated pellets

| | Time/hrs | | | | | | | | | | |
|---|---|---|---|---|---|---|---|---|---|---|---|
| | 0.5 | 1 | 2 | 3 | 4 | 6 | 8 | 10 | 12 | 16 | 18 | 20 |
| (A) % released | 0.7 | 0.6 | 1 | — | 4 | 14 | 26 | 37 | 47 | — | — | 86 |
| SD (%) | 0.3 | 0.5 | 0.6 | | 1 | 1 | 2 | 2 | 2 | | | 2 |
| (B) % released | — | 3 | 4 | 9 | 16 | 29 | 41 | 52 | 63 | 79 | 84 | 87 |
| SD (%) | | 0 | 0 | 0 | 0 | 0 | 0 | 0 | 0 | 0 | 0 | 0 |

Example 5

Preparation of Tablets from Coated Metoprolol Pellets

The coated drug pellets A and B made according to Example 3 were mixed with equal amounts of microcrystalline cellulose, Avicel PH102 in a Turbula mixer T2C (Willy A. Bachofen, Switzerland) for approximately 4 minutes. After addition of 0.15% sodium stearyl fumarate the powder mass was mixed for 2 minutes. After the mixing was ended the mass was compressed to tablets on an excenter press (KilianSP300, Germany) using a pressure of approx. 8 kN. Typical tablet weights were around 200 mg with slightly less than 50 mg metoprolol in each tablet.

Result: No problems were met during the tabletting of the coated pellets.

Example 6

Release of metoprolol from tablets of coated pellets

The release of metoprolol from tablets made according to Example 5 was studied at 37° C. using the USP dissolution apparatus II (rotating paddle) with stirring rate=100 rpm. The release medium was composed of phosphate buffer with the ionic strength=0.1 M and the pH=6.8. Samples were withdrawn for analysis (absorbance of metoprolol at 273 nm in a 1 cm cell). Amounts of released metoprolol were determined from measurements of the absorbance of a standard metoprolol solution based on the same medium as used in the release experiments.

Results:

The amounts of released metoprolol vs time are given in Table 3 referring to the different pellets A and B made according to Example 3. It was found that acceptable release profiles were obtained.

TABLE 3

Release (%) of metoprolol from tablets compressed from coated pellets

| | Time/hrs | | | | | | | | | | |
|---|---|---|---|---|---|---|---|---|---|---|---|
| | 0.5 | 1 | 2 | 3 | 4 | 6 | 8 | 10 | 12 | 16 | 18 | 20 |
| (A) % released | 14 | 19 | 30 | — | 44 | 55 | 64 | 72 | 79 | — | — | 102 |
| SD (%) | 2 | 2 | 2 | | 3 | 4 | 5 | 4 | 5 | | | 4 |
| (B) % released | — | 12 | 23 | 32 | 41 | 51 | 60 | 67 | 73 | 83 | 86 | 89 |
| SD (%) | | 1 | 2 | 3 | 3 | 4 | 4 | 4 | 5 | 5 | 4 | 5 |

The invention claimed is:

1. A composition producing an extended-release film coat when applied to a pharmaceutical formulation, wherein the composition comprises an admixture of the following components:
   a) an ethylacrylate/methylmethacrylate copolymer dispersion,
   b) a surfactant,
   c) sodium stearyl fumarate, and
   d) a water-containing liquid,
and wherein the amount of ethylacrylate/methylmethacrylate copolymer in the film coating composition is in the range of 15 to 50% by weight.

2. The composition as claimed in claim 1, wherein the water-containing liquid is water.

3. The composition as claimed in claim 1, wherein the surfactant is nonoxynol 100.

4. The composition according to claim 1, wherein the surfactant is nonoxynol 100 and the water-containing liquid is water.

5. A process for the preparation of a composition producing an extended-release film coat according to any one of claim 1, 2, 3 or 4, comprising mixing together an ethylacrylate/methylmethacrylate copolymer dispersion, a surfactant, sodium stearyl fumarate and a water-containing liquid at a temperature in the range of 10 to 100° C.

6. An extended-release film coat covering a pharmaceutical core, wherein the core comprises a pharmacologically active ingredient and optionally one or more pharmaceutically acceptable excipients, wherein the film coat comprises an admixture of the following components:
   a) an ethylacrylate/methylmethacrylate copolymer,
   b) a surfactant, and
   c) sodium stearyl fumarate,
and wherein the film coat has been deposited from a water-containing liquid and the amount of the ethylacrylate/methylmethacrylate copolymer in the film coat is in the range of 80 to 99.5% by weight.

7. The film coat according to claim 6, wherein the surfactant is nonoxynol 100.

8. The film coat to claim 6, wherein the surfactant is nonoxynol 100 and the water-containing liquid is water.

9. A process to prepare an extended-release film coat according to any one of claim 6, 7 or 8, comprising the steps:
   a) mixing together an ethylacrylate/methylmethacrylate copolymer dispersion, a surfactant, sodium stearyl fumarate and a water-containing liquid at a temperature in the range of 10 to 100° C. to produce a film coating composition;
   b) depositing the film coating composition on the pharmaceutical core; and
   c) removing the liquid from the film composition.

10. A pharmaceutical formulation comprising:
   a) a pharmaceutical core comprising a pharmacologically active ingredient and optionally one or more pharmaceutically acceptable excipients, and
   b) an extended-release film coat comprising an admixture of the following components:
      i) an ethylacrylate/methylmethacrylate copolymer,
      ii) a surfactant, and
      iii) sodium stearyl fumarate,
   wherein the film coat has been deposited from a water-containing liquid and the amount of the ethylacrylate/methylmethacrylate copolymer in the film coat is in the range of 80 to 99.5% by weight.

11. A process to prepare a formulation as claimed in claim 10, comprising the steps:
   a) mixing together an ethylacrylate/methylmethacrylate copolymer dispersion, a surfactant, sodium stearyl fumarate and a water-containing liquid at a temperature in the range of 10 to 100° C. to produce a film coating composition;
   b) coating the pharmaceutical core with the film coating composition; and
   c) removing the liquid from the film forming composition.

12. A pharmaceutical formulation comprising a pharmacologically active ingredient which is provided in a plurality of beads, wherein the beads optionally contain one or more pharmaceutically acceptable excipients, wherein each bead is coated with an extended-release film coat comprising an admixture of the following components:
   a) an ethylacrylate/methylmethacrylate copolymer,
   b) a surfactant, and
   c) sodium stearyl fumarate,
   and wherein the film coat has been deposited from a water-containing liquid and the amount of the ethylacrylate/methylmethacrylate copolymer in the film coat is in the range of 80 to 99.5% by weight.

13. The formulation according to claim 10 or 12, wherein the pharmacologically active ingredient has activity in the treatment of cardiovascular or gastrointestinal diseases.

14. The formulation according to claim 13, wherein the pharmacologically active ingredient is a beta-blocking adrenergic agent.

15. The formulation according to claim 14, wherein the pharmacologically active ingredient is metoprolol or a pharmaceutically acceptable salt thereof.

16. The formulation according to claim 15, wherein the metoprolol salt is the tartrate, succinate, fumarate or benzoate salt.

17. A process to prepare a formulation as claimed in claim 12, comprising the steps:
   a) mixing together an ethylacrylate/methylmethacrylate copolymer dispersion, a surfactant, sodium stearyl fumarate and a water-containing liquid at a temperature in the range of 10 to 100° C. to produce a film coating composition;
   b) coating the plurality of beads with the film coating composition; and
   c) removing the liquid from the film forming composition.

18. The formulation according to claim 10 or 12, wherein the surfactant is nonoxynol 100.

19. The formulation of claim 10 or 12, wherein the surfactant is nonoxynol 100 and the water-containing liquid is water.

20. The formulation according to claim 10 or 12, wherein the pharmacologically active ingredient has activity in the treatment of cardiovascular or gastrointestinal diseases.

21. The formulation according to claim 20, wherein the pharmacologically active ingredient is a beta-blocking adrenergic agent.

22. The formulation according to claim 21, wherein the pharmacologically active ingredient is metoprolol or a pharmaceutically acceptable salt thereof.

23. The formulation according to claim 22, wherein the metoprolol salt is the tartrate, succinate, fumarate or benzoate salt.

24. A composition producing an enteric film coat when applied to a pharmaceutical formulation, wherein the composition comprises an admixture of the following components:
   a) an ethylacrylate/methylmethacrylate copolymer dispersion,
   b) a surfactant,
   c) sodium stearyl fumarate, and
   d) a water-containing liquid,
   and wherein the amount of ethylacrylate/methylmethacrylate copolymer in the film coating composition is in the range of 15 to 50% by weight.

25. An enteric film coat covering a pharmaceutical core, wherein the core comprises a pharmacologically active ingredient and optionally one or more pharmaceutically acceptable excipients, wherein the film coat comprises an admixture of the following components:
   a) an ethylacrylate/methylmethacrylate copolymer,
   b) a surfactant, and
   c) sodium stearyl fumarate,
   and wherein the film coat has been deposited from a water-containing liquid and the amount of the ethylacrylate/methylmethacrylate copolymer in the film coat is in the range of 80 to 99.5% by weight.

26. The film coat according to claim 6 or 25, wherein the amount of surfactant is in the range of 0.05 to 12% by weight.

27. The film coat according to claim 6 or 25, wherein the amount of sodium stearyl fumarate is in the range of 0.05 to 12% by weight.

28. A pharmaceutical formulation comprising:
   a) a pharmaceutical core comprising a pharmacologically active ingredient and optionally one or more pharmaceutically acceptable excipients, and
   b) an enteric film coat comprising an admixture of the following components:
      i) an ethylacrylate/methylmethacrylate copolymer,
      ii) a surfactant, and
      iii) sodium stearyl fumarate,
   wherein the film coat has been deposited from a water-containing liquid and the amount of the ethylacrylate/methylmethacrylate copolymer in the film coat is in the range of 80 to 99.5% by weight.

29. A pharmaceutical formulation comprising a pharmacologically active ingredient which is provided in a plurality of beads, wherein the beads optionally contain one or more pharmaceutically acceptable excipients, wherein each bead is coated with an enteric film coat comprising an admixture of the following components:
a) an ethylacrylate/methylmethacrylate copolymer,
b) a surfactant, and
c) sodium stearyl fumarate, and wherein the film coat has been deposited from a water-containing liquid and the amount of the ethylacrylate/methylmethacrylate copolymer in the film coat is in the range of 80 to 99.5% by weight.

* * * * *